United States Patent
Rocco et al.

(10) Patent No.: US 11,860,124 B2
(45) Date of Patent: *Jan. 2, 2024

(54) OIL DEBRIS MONITOR TO DETECT MECHANICAL FAILURES IN HIGH NOISE ENVIRONMENTS

(71) Applicant: RTX Corporation, Farmington, CT (US)

(72) Inventors: Edward Thomas Rocco, Rocky Hill, CT (US); Danbing Seto, Avon, CT (US)

(73) Assignee: RTX Corporation, Farmington, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/666,009

(22) Filed: Feb. 7, 2022

(65) Prior Publication Data

US 2022/0155257 A1    May 19, 2022

Related U.S. Application Data

(63) Continuation of application No. 16/385,157, filed on Apr. 16, 2019, now Pat. No. 11,268,932.

(51) Int. Cl.
G01N 27/74 (2006.01)
G01N 33/28 (2006.01)
G01N 27/02 (2006.01)

(52) U.S. Cl.
CPC .......... *G01N 27/74* (2013.01); *G01N 33/2888* (2013.01)

(58) Field of Classification Search
CPC .... G01N 33/2888; G01N 27/02; G01N 29/02; G01N 33/2858; G01N 21/85
See application file for complete search history.

(56) References Cited

U.S. PATENT DOCUMENTS

| 8,522,604 B2 * | 9/2013 | Zhe ........................ G01M 13/02 73/53.07 |
| 2003/0102854 A1 * | 6/2003 | Gascoyne .......... G01N 15/1218 324/71.4 |

(Continued)

FOREIGN PATENT DOCUMENTS

| CA | 2639710 A1 | 3/2010 |
| CN | 104792668 A | 7/2015 |
| CN | 109283102 A | 1/2019 |

OTHER PUBLICATIONS

EP Search Report dated Sep. 30, 2020 issued for corresponding European Patent App. No. 20169816.4.

*Primary Examiner* — Jermele M Hollington
*Assistant Examiner* — Temilade S Rhodes-Vivour
(74) *Attorney, Agent, or Firm* — Bachman & LaPointe, P.C.

(57) ABSTRACT

A method to effectively utilize an oil debris monitor to provide advanced warning to mechanical system failures in a high noise system by adapting detection and annunciation algorithms to the background noise in a system that includes collecting I and Q channel data from a sensor; processing the I and Q channel data to both calculate a noise based (RMS adjusted) detection threshold and to identify a ferrous and nonferrous signal; processing the ferrous and nonferrous signals to determine signal peaks above the RMS adjusted detection threshold; adjusting a detection threshold if more signal peaks observed than allowable particles in a given time window; transmitting the detection threshold previously determined to particle detection, rate limit adjustment, detectability algorithms, and estimated mass loss accumulation.

18 Claims, 15 Drawing Sheets

(56) References Cited

U.S. PATENT DOCUMENTS

| | | |
|---|---|---|
| 2010/0109686 A1 | 5/2010 | Zhe |
| 2011/0224917 A1 | 9/2011 | Uluyol |
| 2012/0025529 A1 | 2/2012 | Davis |
| 2012/0046896 A1* | 2/2012 | Flandrois ............... G01N 27/10 702/65 |
| 2012/0117945 A1* | 5/2012 | Krafthefer .............. F01N 11/00 60/277 |
| 2012/0130617 A1* | 5/2012 | Raimarckers ........... F01D 25/18 701/99 |
| 2013/0000376 A1 | 1/2013 | Allam |
| 2013/0080085 A1* | 3/2013 | Von Herzen ........... G01N 33/30 702/50 |
| 2014/0130587 A1* | 5/2014 | Von Herzen ....... G01N 33/2888 73/114.55 |
| 2015/0293009 A1* | 10/2015 | Henning ............ G01N 33/2858 356/72 |
| 2017/0248572 A1 | 8/2017 | Byington |
| 2018/0023414 A1* | 1/2018 | Hagen ....................... F02C 7/06 73/53.05 |
| 2018/0231497 A1 | 8/2018 | Glaberson |

* cited by examiner

OIL DEBRIS MONITOR TO DETECT MECHANICAL FAILURES IN HIGH NOISE ENVIRONMENTS

CROSS-REFERENCE TO RELATED APPLICATION

This application is a continuation of co-pending U.S. patent application Ser. No. 16/385,157, filed Apr. 16, 2019.

BACKGROUND

The present disclosure relates to an oil system for a rotating machinery such as a gas turbine engine and, more particularly, to an on-board debris detection system that adapts to noises.

Many types of mechanical machinery include various components that require lubrication. Gas turbine engines, for example, typically include gears and bearings that require a lubricating liquid, such as oil, for lubrication and cooling during operation. When an oil wetted component has a mechanical failure, metallic debris may be released into the lubricating liquid. In order to receive advanced warning of these mechanical systems failures for the purpose of condition based maintenance, lubrication systems may include an oil debris monitoring system to sense metallic debris in the oil. An oil debris monitor system is used to flag the initiation or progression of mechanical failures in the lubricated mechanical machinery.

Metallic debris, measured by the counts and mass of particles detected by the oil debris monitor sensor, is processed and monitored by a controller, and when debris is released at a critical rate, an alert is produced; driving field troubleshooting and corrective action. While the oil debris monitor sensing technology is well developed, its application in aerospace systems, such as gas turbine engines, is much challenged due to the stringent requirements on fault detection and the environment the sensor is operating in. Today's aerospace systems are often built with great sophistication and little margin, which require the fault detection to be early, accurate and reliable. For mechanical failures in gas turbine engine applications, detection of fine particles (a few hundred microns) is required. Furthermore, the operating environment (vibration, pressure pulsations, aeration, etc.) can induce noise in oil debris monitor signals. Sensor and harness deterioration in response to harsh operating environments will also produce additional noises in oil debris monitor signals. Electromagnetic and/or Magnetic Interferences will disturb the oil debris monitor signals as well. Excessive noises lead to misdetection of mechanical failures and false positive alerts. All of these challenges call for a more effective utilization of oil debris monitoring sensing system.

SUMMARY

A method for determining a detection threshold used for determining the presence of a particle in a system according to one disclosed non-limiting embodiment of the present disclosure includes a) collecting I and Q channel data from a sensor; b) calculating a detection threshold based on a measure of background noise in the system; c) processing the I and Q channel data to identify a ferrous and nonferrous signal; d) processing the ferrous and nonferrous signals to determine signal peaks above an RMS adjusted detection threshold; e) adjusting a detection threshold if more signal peaks are observed than allowable particles in a given time window; and f) transmitting the detection threshold determined in step e).

A further aspect of the present disclosure includes converting the I and Q channel data to digital I and Q data within a controller on-board an aircraft.

A further aspect of the present disclosure includes continually filling a buffer of the controller with the I and Q channel data.

A further aspect of the present disclosure includes that the sensor is an oil debris monitor sensor.

A further aspect of the present disclosure includes that step e) comprises transmitting the detection threshold to a particle detection algorithm.

A further aspect of the present disclosure includes that step e) comprises transmitting the detection threshold to a rate limit algorithm.

A further aspect of the present disclosure includes that step e) comprises transmitting the detection threshold to a detectability calculation algorithm.

A further aspect of the present disclosure includes that step c) comprises processing the ferrous and nonferrous signals to determine signal peaks above C*RMS of the ODM I,Q signals.

A further aspect of the present disclosure includes that C is a calculated constant determined by analyzing system data to determine how an adjusted threshold would impact the particle detection threshold.

A further aspect of the present disclosure includes that C is 2.5 to 4.

A further aspect of the present disclosure includes that the RMS calculation using the raw I and Q data is determined in a fixed time window.

A further aspect of the present disclosure includes f) receiving the calculated detection threshold; g) identifying a rate limit as a function of the calculated detection threshold; h) calculating a rate limit influence factor; i) summing a discrete rate limit influence continuously over a window to calculate the rate limit; j) transmitting the calculated rate limit to a particle release rate comparison algorithm; and k) generating an alert if the calculated rate limit is below an acceptable limit.

A further aspect of the present disclosure includes f) receiving the calculated detection threshold; g) calculating a time spent above a critical detection threshold; h) weigh the time spent above a critical detection threshold by detection threshold; i) calculating a detectability from steps f)-h) as the percent of weighted time spent below a critical detection threshold; j) generating an alert if the detectability is below an acceptable limit.

A further aspect of the present disclosure includes f) receiving the calculated detection threshold; g) identifying a ratio of particles detected, $\delta RD_i$, associated with the detection threshold; h) calculating the average of particles detected over a time window of interest; i) estimating accumulated particles from steps g)-h); and j) communicating an estimated particle count from step i) to a rate limit algorithm.

A further aspect of the present disclosure includes f) receiving the calculated detection threshold; g) identifying a ratio of particles detected, $\delta RD_i$, associated with the detection threshold; h) calculating the average of particles detected over a time window of interest; i) estimating accumulated particles from steps g)-h); j) converting the accumulated particles to mass loss; k) accumulating the mass loss within a flight; l) accumulating the mass loss across multiple flight in Non-Volatile Memory; m) setting a fault flag when the accumulated mass loss exceed a predefined limit; n) alerting mechanical failure if mass loss exceedance and/or particle rate limit exceedance occur; and o) resetting the mass loss accumulation once the fault alert is cleared.

An oil system for a gas turbine engine according to one disclosed non-limiting embodiment of the present disclosure includes an oil flow path; an in-line oil debris monitor sensor; and a control system in communication with the in-line oil debris monitor sensor to determine whether a particle is present, a detection threshold for presence of the particle determined as a function of background noise.

A further aspect of the present disclosure includes that the oil flow path is in communication with a geared architecture of the gas turbine engine.

A further aspect of the present disclosure includes that the system will issue a health warning when the detection threshold is below a calculate value.

A further aspect of the present disclosure includes that a rate limit is determined from a look up table as a function of the detection threshold.

A further aspect of the present disclosure includes a method of estimating a particle accumulation, comprising: receiving a calculated detection threshold; identifying a ratio of particles detected, $\delta RD_i$, associated with the detection threshold; calculating the average ratio of particles detected over a time window of interest; estimating accumulated particles from the identifying and the calculating steps; and communicating the estimated particle accumulation to a rate limit algorithm.

A further aspect of the present disclosure includes a method of monitoring a sensing system, comprising: receiving a calculated detection threshold; calculating a time spent above a critical detection threshold; weighing the time spent above a critical detection threshold by detection threshold; calculating a detectability as the percent of weighted time spent below the critical detection threshold; and generating an alert if the detectability is below an acceptable limit.

A further aspect of the present disclosure includes a method of monitoring an oil system, comprising: receiving a calculated detection threshold; identifying a ratio of particles detected, $\delta RD_i$, associated with the detection threshold; calculating the average of particles detected over a time window of interest; estimating accumulated particles from the identifying and the calculating steps; converting the accumulated particles to mass loss; accumulating the mass loss within a flight; accumulating the mass loss across multiple flight in Non-Volatile Memory; setting a fault flag when the accumulated mass loss exceeds a predefined limit; alerting mechanical failure if mass loss exceedance and/or particle rate limit exceedance occur; and resetting the mass loss accumulation once the fault alert is cleared.

The foregoing features and elements may be combined in various combinations without exclusivity, unless expressly indicated otherwise. These features and elements as well as the operation thereof will become more apparent in light of the following description and the accompanying drawings. It should be appreciated; however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
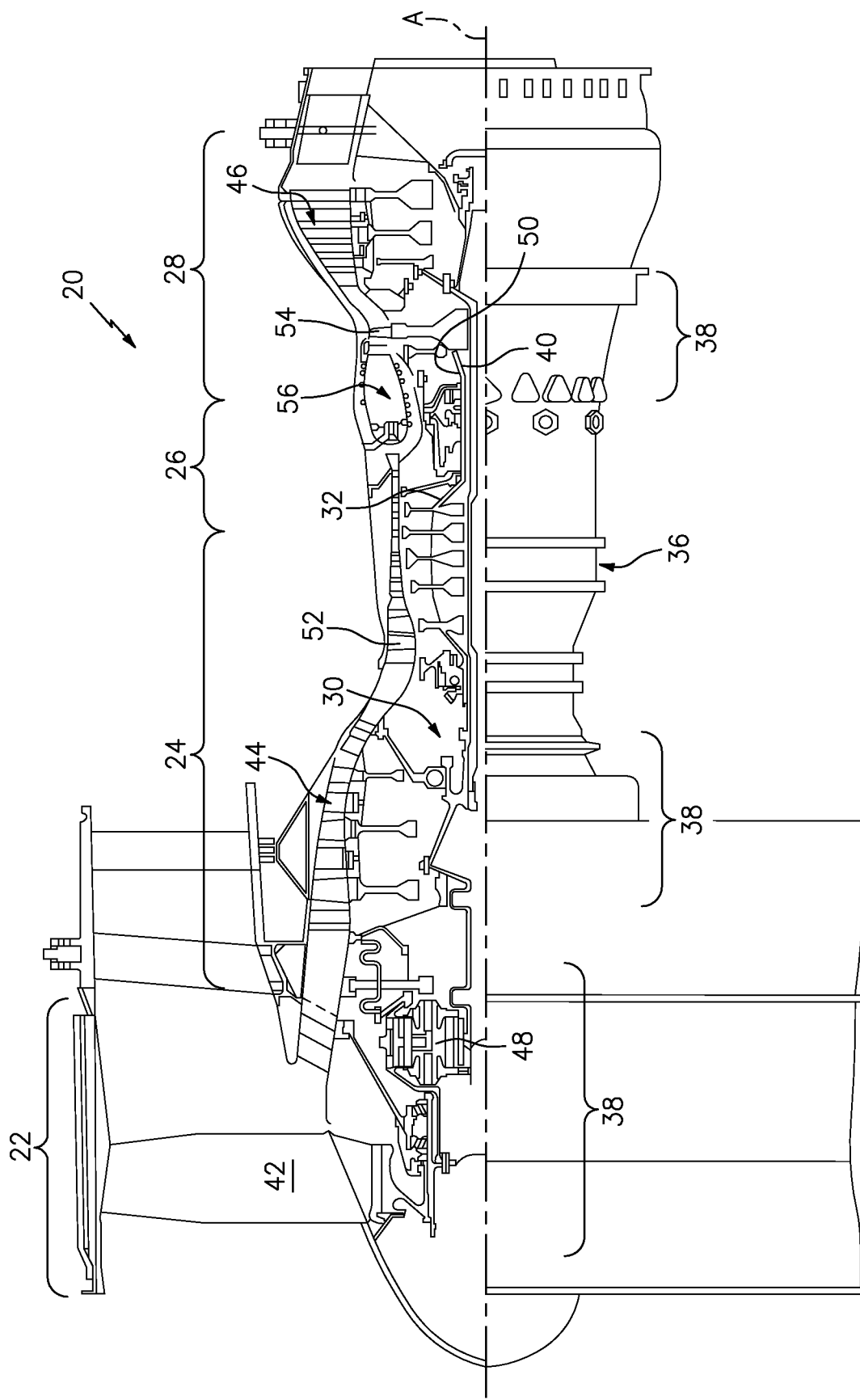
FIG. 1 is a schematic cross-section of an example gas turbine engine architecture.

FIG. 1 schematically illustrates a gas turbine engine 20. The gas turbine engine 20 is disclosed herein as a two-spool turbofan that generally incorporates a fan section 22, a compressor section 24, a combustor section 26, and a turbine section 28. The fan section 22 drives air along a bypass flowpath while the compressor section 24 drives air along a core flowpath for compression and communication into the combustor section 26, then expansion through the turbine section 28. Although depicted as a turbofan in the disclosed non-limiting embodiment, it should be appreciated that the concepts described herein may be applied to other engine architectures such as turbojets, turboshafts, and three-spool (plus fan) turbofans.

The engine 20 generally includes a low spool 30 and a high spool 32 mounted for rotation about an engine central longitudinal axis A relative to an engine static structure 36 via several bearings 38. The low spool 30 generally includes an inner shaft 40 that interconnects a fan 42, a low pressure compressor ("LPC") 44 and a low pressure turbine ("LPT") 46. The inner shaft 40 drives the fan 42 directly or through a geared architecture 48 that drives the fan 42 at a lower speed than the low spool 30. An exemplary reduction transmission is an epicyclic transmission, such as a planetary or star gear system.

The high spool 32 includes an outer shaft 50 that interconnects a high pressure compressor ("HPC") 52 and high pressure turbine ("HPT") 54. A combustor 56 is arranged between the high pressure compressor 52 and the high pressure turbine 54. The inner shaft 40 and the outer shaft 50 are concentric and rotate about the engine central longitudinal axis A which is collinear with their longitudinal axes.

Core airflow is compressed by the LPC 44, then the HPC 52, mixed with the fuel and burned in the combustor 56, then expanded over the HPT 54 and the LPT 46 which rotationally drive the respective high spool 32 and the low spool 30 in response to the expansion. The shafts 40, 50 are supported at a plurality of points by bearings 38 within the static structure 36.

Figure 2:
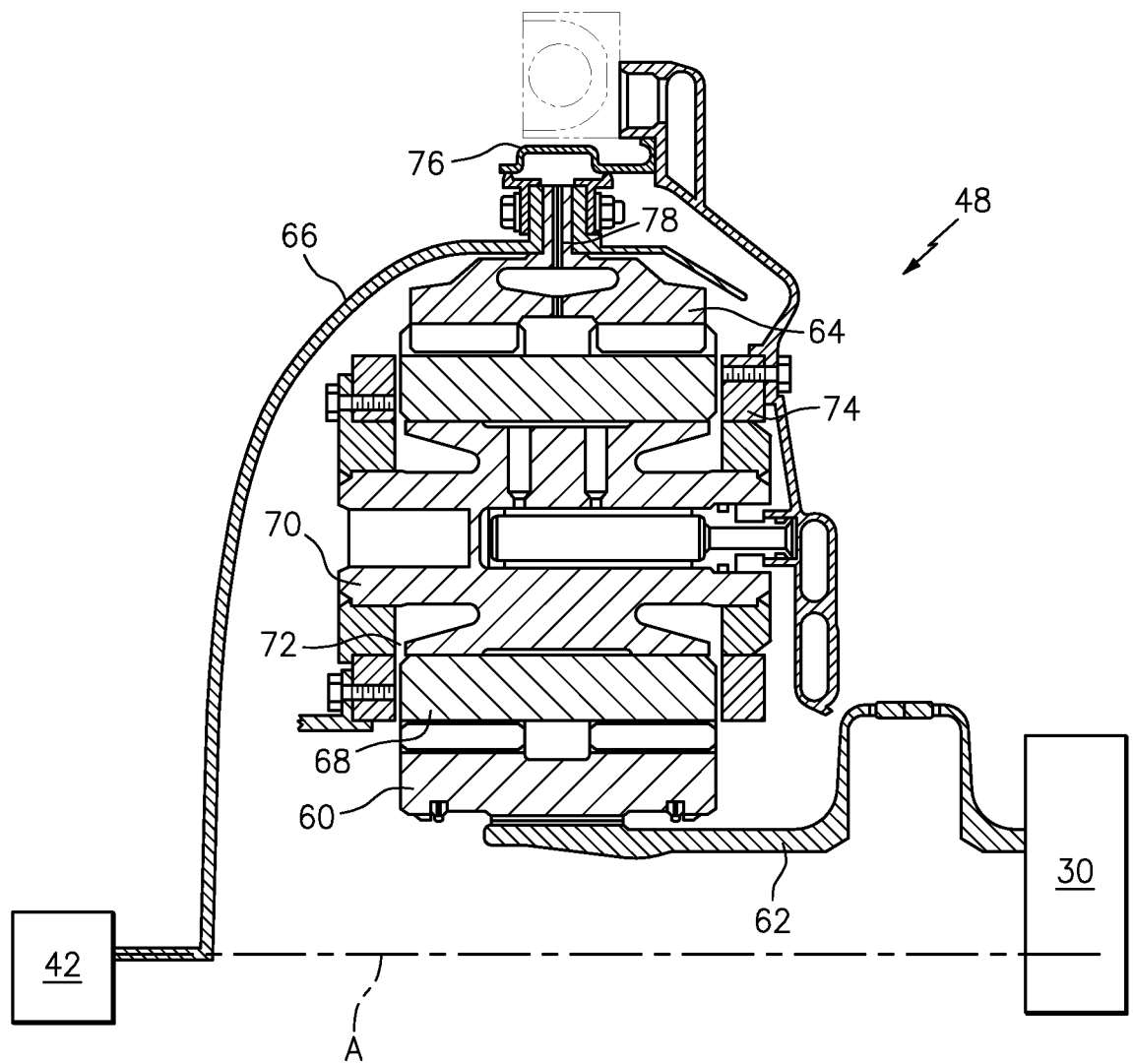
FIG. 2 is a schematic cross-section of a geared architecture for a gas turbine engine.

With reference to FIG. 2, the geared architecture 48 includes a sun gear 60 driven by a sun gear input shaft 62 from the low spool 30, a ring gear 64 connected to a ring gear output shaft 66 to drive the fan 42 and a set of intermediate gears 68 in meshing engagement with the sun gear 60 and ring gear 64. Each intermediate gear 68 is mounted about a journal pin 70 which are each respectively supported by a carrier 74. The input shaft 62 and the output shaft 66 counter-rotate as the sun gear 60 and the ring gear 64 are rotatable about the engine central longitudinal axis A. The carrier 74 is grounded and non-rotatable even though the individual intermediate gears 68 are each rotatable about their respective axes 80. An oil recovery gutter 76 is located around the ring gear 64. The oil recovery gutter 76 may be radially arranged with respect to the engine central longitudinal axis A.

A replenishable film of oil, not shown, is supplied to an annular space 72 between each intermediate gear 68 and the respective journal pin 70. One example applicable oil meets U.S. Military Specification MIL-PRF-23699, for example, Mobil Jet Oil II manufactured by ExxonMobil Aviation, United States. Oil is supplied through the carrier 74 and into each journal pin 70 to lubricate and cool the gears 60, 64, 68 of the geared architecture 48. Once communicated through the geared architecture 48 the oil is radially expelled through the oil recovery gutter 76 in the ring gear 64 by various paths such as oil passage 78.

Figure 3:
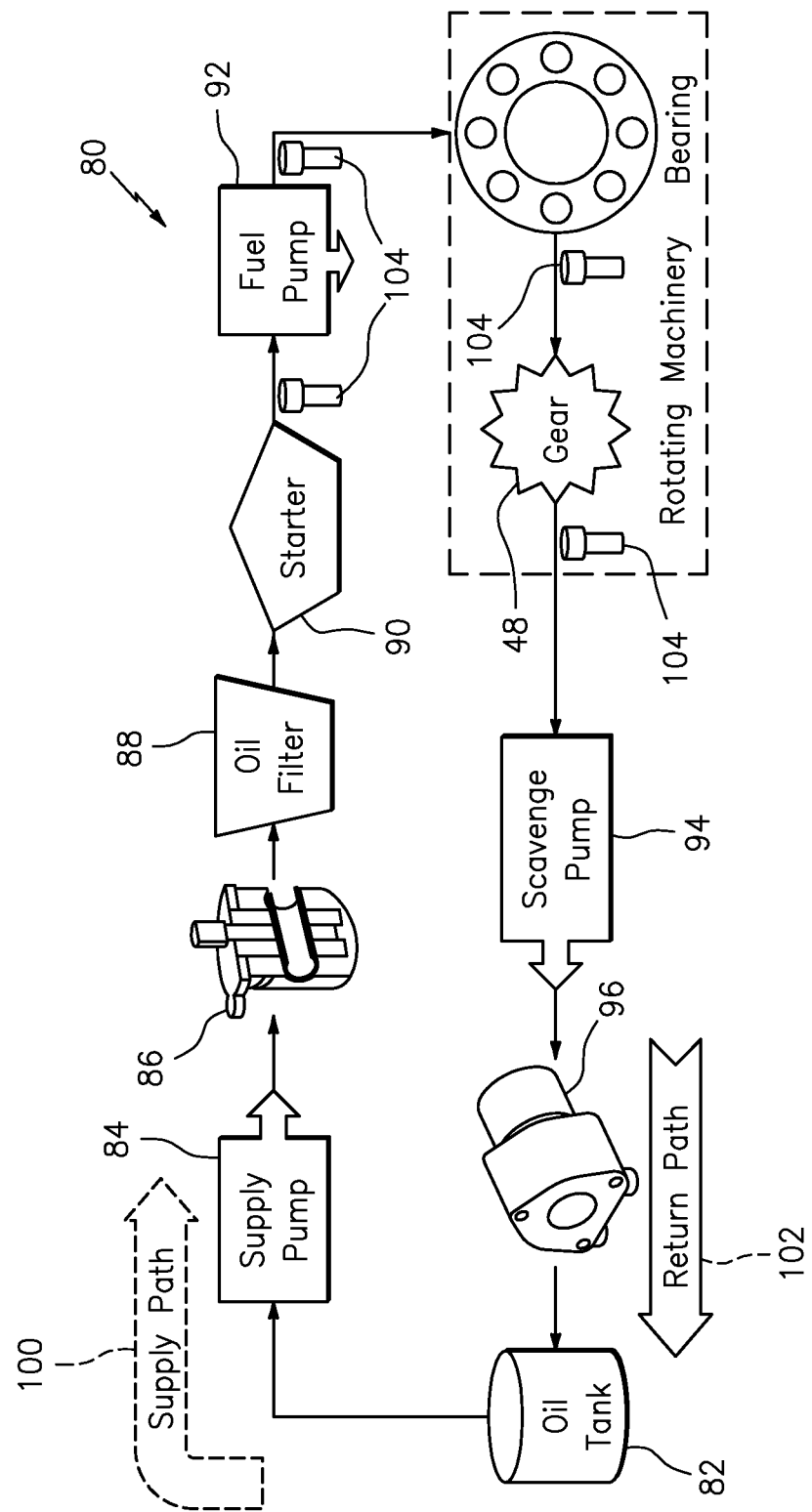
FIG. 3 is a schematic diagram of an oil system for a geared architecture gas turbine engine.

With reference to FIG. 3, an oil system 80 is schematically illustrated in block diagram form for the geared architecture 48 as well as other components which receive oil. It should be appreciated that the oil system 80 is but a schematic illustration and is simplified in comparison to an actual oil system. The oil system 80 generally includes an oil tank 82, a supply pump 84, an oil debris monitoring sensor 86, an oil filter 88, a starter 90, a fuel pump 92, the geared and bearing architecture 48, a scavenge pump 94, and an oil debris monitoring sensor 96 at an alternative location. The oil debris monitoring sensor 86, 96 could be a single sensor or a set of sensors placed in branched oil paths. The oil flow to the geared and bearing architecture 48 may be considered an oil supply path 100, and the oil flow from the geared and bearing architecture 48 can be considered an oil return path 102. Multiple of chip collectors 104 may be located in the supply path 100 and the return path 102 to capture ferrous debris.

The sensors 86, 96 may utilize two field coils, excited by high frequency alternating current, to cause equal and opposing magnetic fields (M-field). The ferrous particle strength of the M-field created by one field coil after another, causes the processed signal to be a period of a sine wave. The nonferrous particle weakens the M-field created by one field coil after another, causing the similar sine wave but in opposing polarity. Generally, the signal magnitude is proportional to the size of particle and the signal width is inversely proportional to the particle speed.

Figure 4:
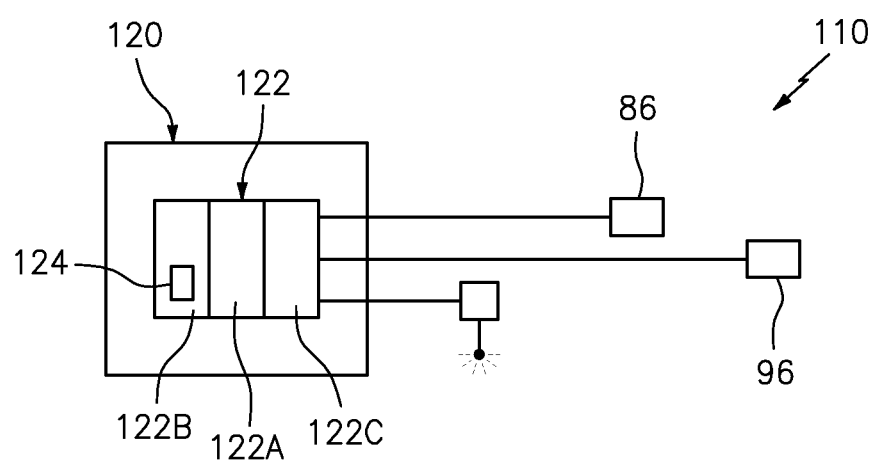
FIG. 4 is a schematic diagram of a debris detection system according to one disclosed non-limiting embodiment.

With Reference to FIG. 4, a debris detection system 110 generally includes a controller 120 in communication with the sensors 86, 96. The sensors 86, 96 may be in-line oil debris monitor sensors. The debris detection system 110 protects against unexpected phase angle changes which may affect individual oil debris monitors caused by replacement or redesign of other components in the system, such as a signal wire harness, that can drastically influence the phase angle.

The controller 120 generally includes a control module 122 that executes logic 124 (FIG. 4) to actively calculate and monitor the oil debris liberated in the oil system with regards to particle detection, mechanical system fault alert, and sensing system health. The functions of the logic 124 are disclosed in terms of functional block diagrams, and it should be appreciated that these functions may be enacted in either dedicated hardware circuitry or programmed software routines capable of execution in a microprocessor-based electronics control embodiment. In one example, the control module 122 may be a portion of a flight control computer, a portion of a Full Authority Digital Engine Control (FADEC), a stand-alone unit, or other system.

The control module 122 typically includes a processor 122A, a memory 122B, and an interface 122C. The processor 122A may be any type of known microprocessor having desired performance characteristics. The memory 122B may be any computer readable medium which stores data and control algorithms such as the logic 124 as described herein. The interface 122C facilitates communication with other components such as the sensors 86, 96, as well as remote systems such as a ground station, Health and Usage Monitoring Systems (HUMS), or other system.

The oil debris monitor phase angle is used to classify detected particle types (ferrous/nonferrous) through a mathematical transformation. The phase angle is calibrated by pulling a particle of known type and size through the sensor and using the ratio of I and Q channel amplitude and trigonometric relationships to calculate an optimum (for classification) phase angle. The I channel is the In-phase, or real component and the Q channel is the Quadrature (90° shift of real component). As will be further described below, this principle is applied to background noise in the debris detection system 110 by calculating the slope of the relationship between noise peaks of the oil debris monitor I and Q data channels. The background noise can be anything in the signal that is not a particle but originated from the sensor, for example, engine vibration induced noises.

Figure 5:
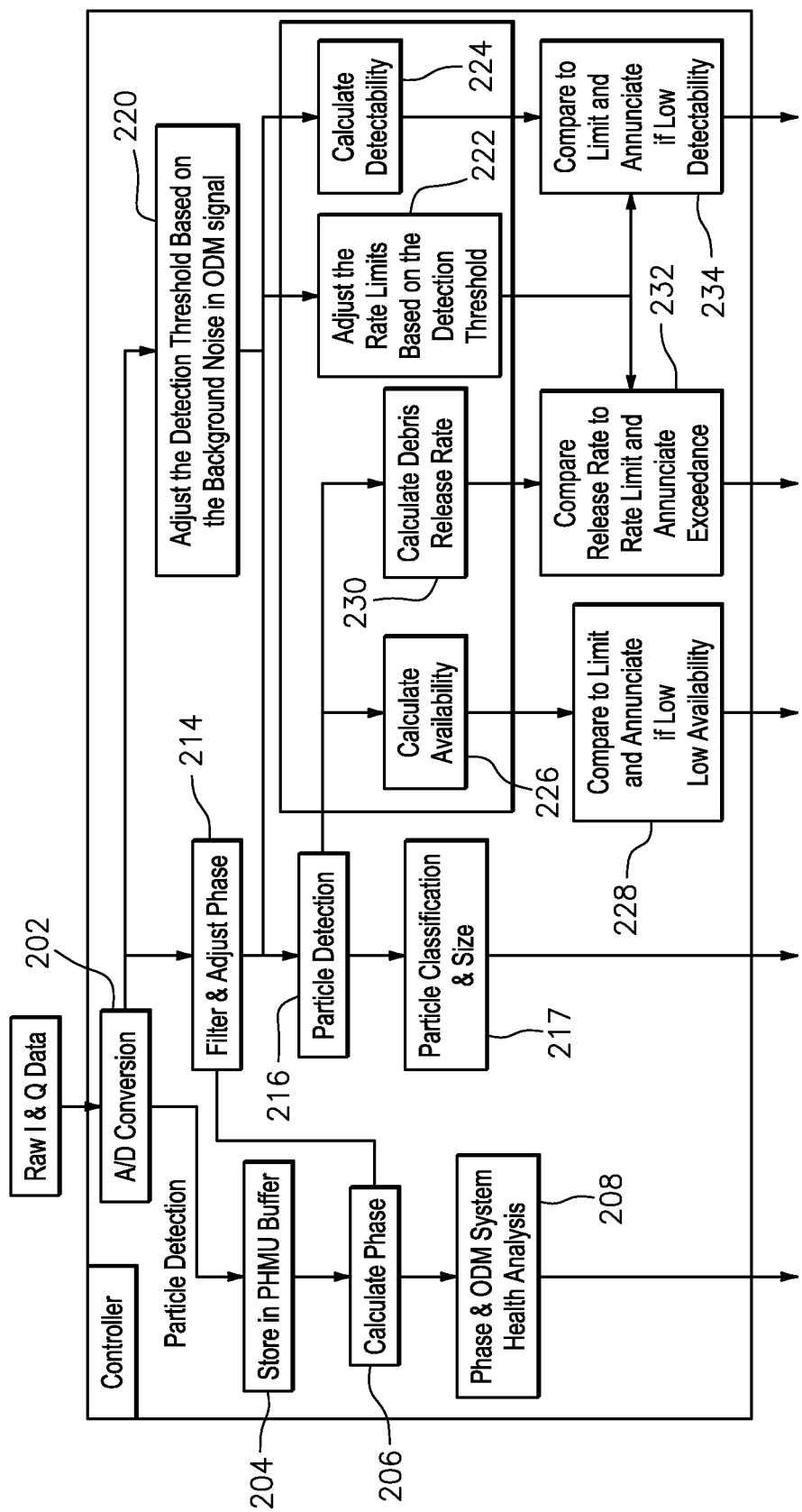
FIG. 5 is a block diagram representative of logic for the debris monitoring system.

With reference to FIG. 5, the logic 124 of the debris detection system 110 initially includes receipt of raw oil debris monitor data from either the sensors 86, 96 into the controller for signal conversion from analog to digital (202). The raw data is stored in a controller buffer (204). The buffer for the controller is continually filled with raw data that flows as a constant stream such that a running on-board algorithm may be performed.

The phase angle of the signal (206) may be calculated from the noise using the raw oil debris monitor data in the controller buffer. The phase angle may then be used for a system health assessment (208) and may be transmitted (210) for further processing in the controller as well as transmitted with system health data for off-board health monitoring (212).

The mechanical system health assessment may include, for example, particle count, particle type classification, size and mass estimates, sensing system availability, debris count rates, and other metrics. The A/D converted raw oil debris monitor signals are filtered and phase angle adjusted (214) within the controller, then the particle detection algorithm executes (216). Typically, the particle signal will distribute into both I and Q channels due to phase angle misalignment between the drive signal and mixer signal as caused by system impedance in the driving and sensing circuitry. The phase angle adjustment realigns the particle signal distribution such that the ferrous particle signal is maximized in the ferrous channel and the nonferrous particle signal is maximized in then nonferrous channel. The particle classification and size data from the particle detection algorithm is then transmitted (218) for off-board health monitoring.

Figure 6:
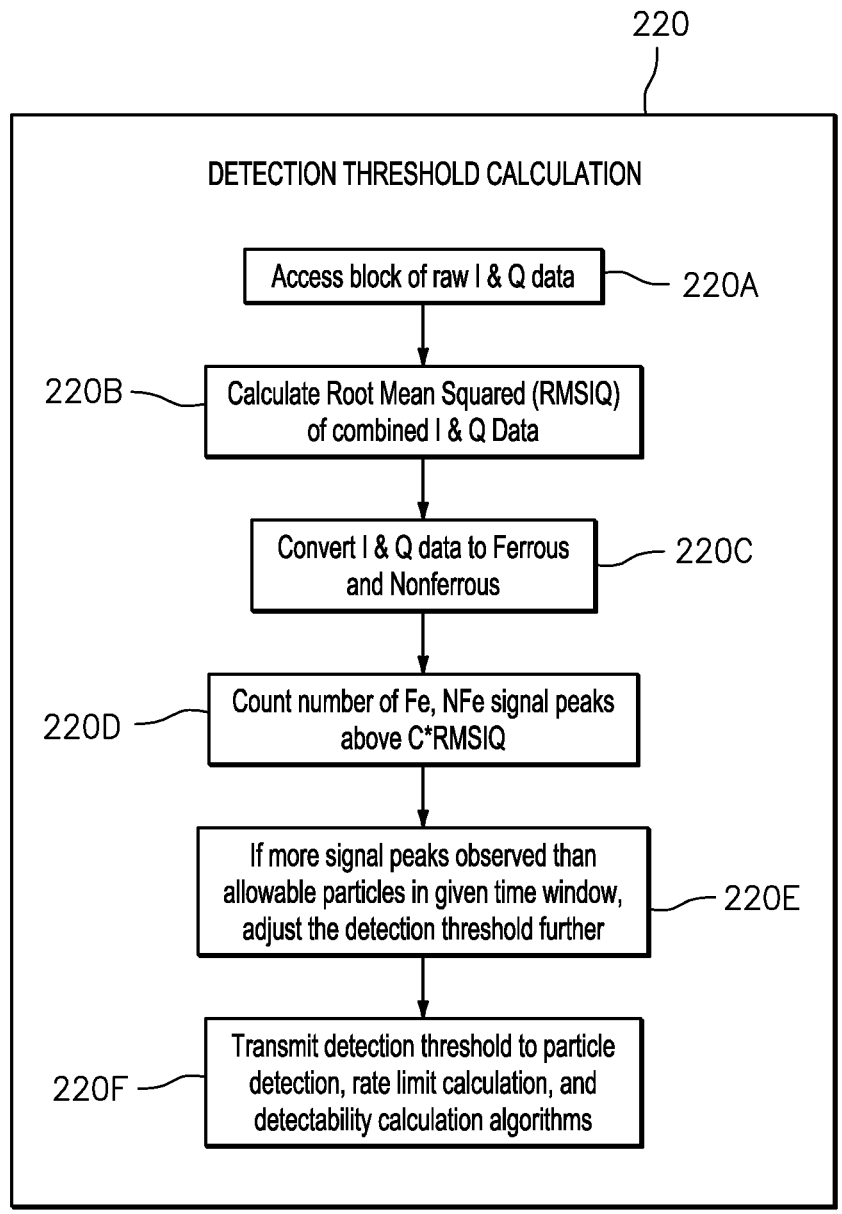
FIG. 6 is a representation of the detection threshold calculation performed in FIG. 5.

The raw data from the conversion of analog to digital (202) is communicated to a module that calculates the particle detection threshold (220; FIG. 6) based on the signal noise level to adjust the detection threshold based on the background noise in the raw ODM channel data. With reference also to FIG. 6, the particle detection threshold (220) is determined from a signal root mean square (RMS) calculation (220B) using the raw I and Q data in a fixed time window. The baseline threshold from the ferrous channel and the nonferrous channel (220C) is adapted to C*RMSIQ (220D), where C is a predefined constant determined by analyzing system data to determine how the particle detection threshold should be adjusted to combat the background noises. In one example, a range for C is 2.5 to 4.

The detection threshold can be further adjusted to avoid short duration, high amplitude signal anomalies. In a given system where analysis is occurring on short duration block of data on the order of less than a second, one can expect a maximum particle pass frequency during that time window (220E). For example, if processing is done on 1 second blocks, and the maximum particle rate is 2 Hz, a maximum of 4 peaks are expected in a block. If more than 4 peaks exceeding the RMS calculated detection threshold, the threshold should be adjusted to the 5th peak. This will reduce the risk of rejecting large particles, and prevent reduced availability due to signal anomalies.

Figure 7:
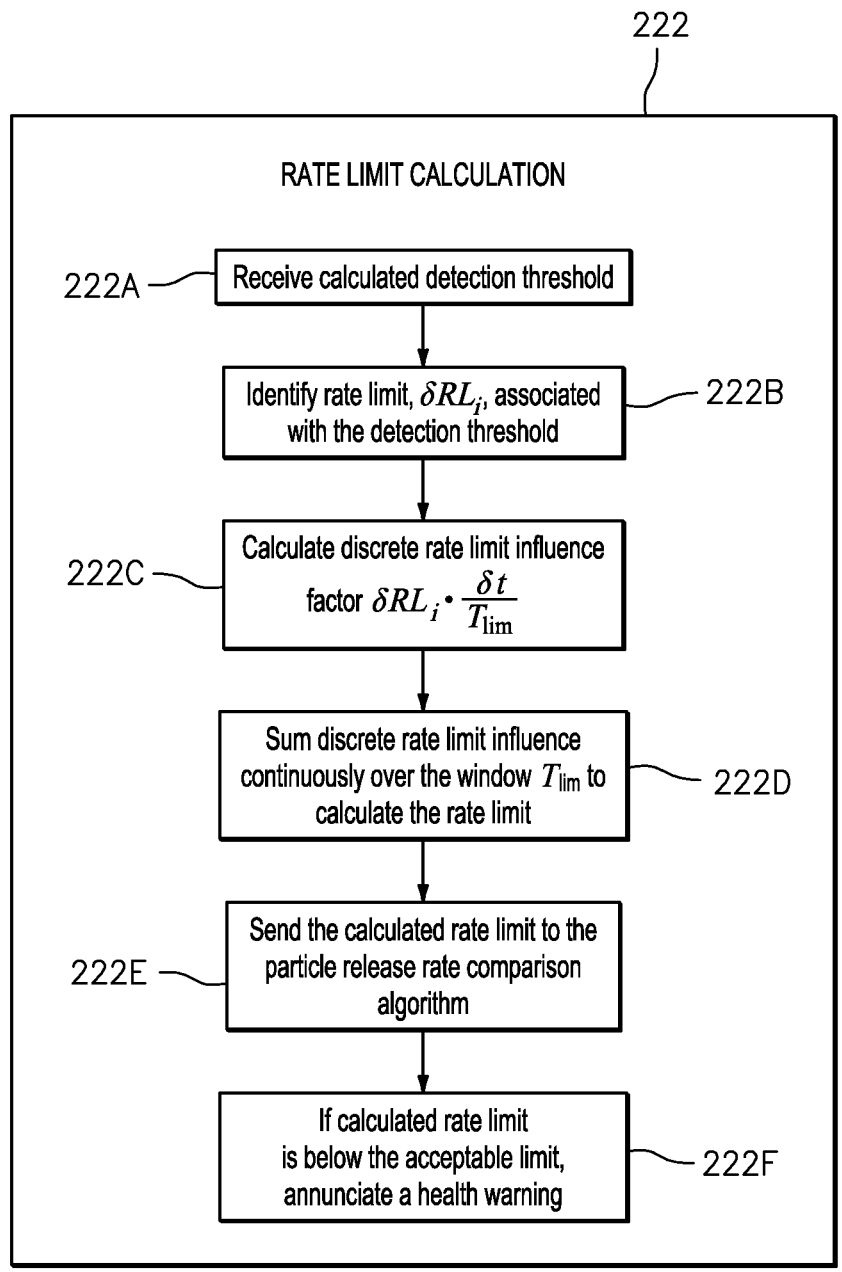
FIG. 7 is a representation of the rate limit calculation performed in FIG. 5.

With reference also to FIG. 7, the rate limit, or maximum number of particles allowed over a given window of time without flagging an alarm, are reduced given a high noise environment. This is necessary, because if the detection threshold of the system is increased, some portion of the failure mode is no longer visible to the sensor. An increased detection threshold alone risks missed detection of progressing failures. Making the rate limit as a function of the detection threshold, or more specifically, reducing the rate limit as the detection threshold increases, mitigates this risk. The rate limit reduction is performed by establishing a relationship between detection threshold (220F) and rate limit (222B) assuming that the calculated detection threshold was a constant in the time window where the rate limit is computed. This relation is also determined using knowledge of expected mechanical failure modes. In a dynamic system the detection threshold, however, will not be constant. Every block of data will have a unique detection threshold, and thus a unique detection threshold influence factor (rate limit for the given detection threshold multiplied by the ratio of time in a given block over the total evaluation period). These unique threshold influence coefficients are summed (222B-D) such that every block of data has an equal influence on the net rate limit. Given the expected particle distributions for a failure mode, there will be a minimum acceptable calculated rate limit (222E) to reliably detect failure modes without creating a nuisance. If the calculated rate limit falls below the minimum acceptable limit, an alert will be issued to indicate maintenance of the sensing system is required and one or more components in the sensing systems 86, 96 needs to be replaced.

Figure 8:
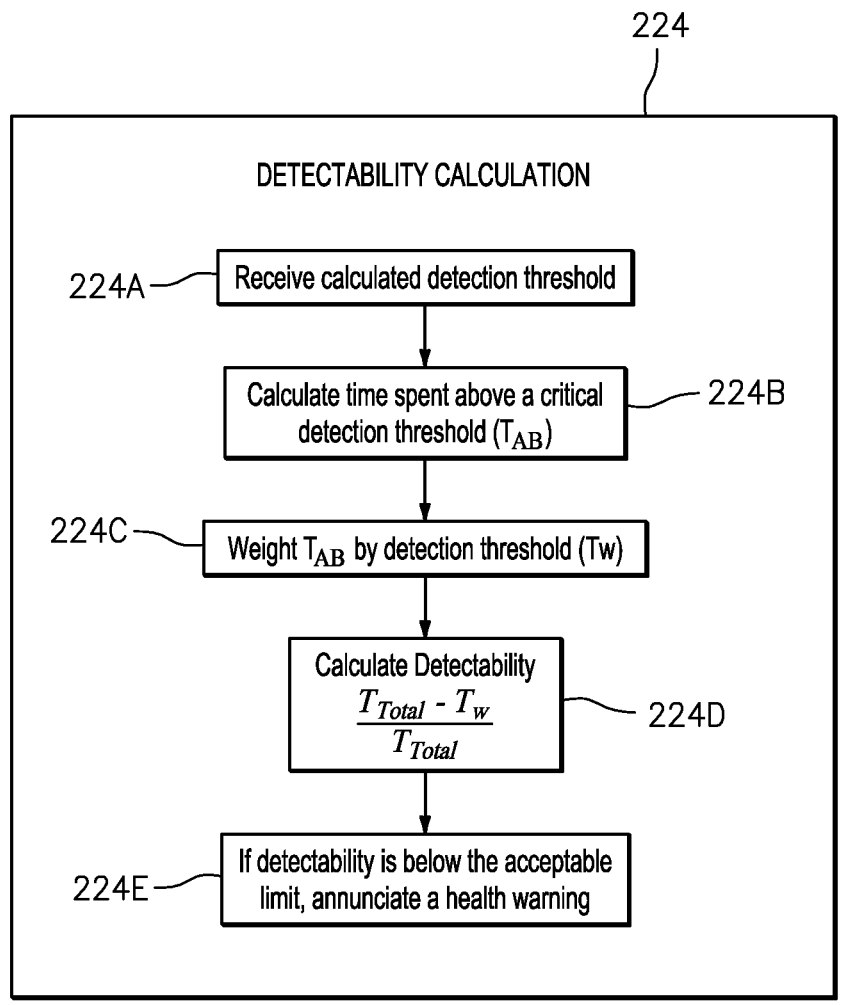
FIG. 8 is a representation of the detectability calculation performed in FIG. 5.

With reference also to FIG. 8, if the noise in the debris detection system 110 is very high, detection capability is reduced. To prevent the debris detection system 110 from spending too much time at the elevated noise levels, a critical detection threshold should be established. The amount of time spent above this threshold will be accumulated (224A). Detectability is then calculated as the ratio of time spent with a calculated threshold below the critical detection threshold. The time above the critical threshold (224B) can also be weighted (224C) so that a significant threshold exceedance impacts the detectability more than a minor exceedance (i.e., if the limit were 120 millivolts, the calculation can be weighted such that 1 second with a threshold at 250 millivolts is equivalent to 10 seconds with a threshold at 125 millivolts, since the former condition is much more severe). If the calculated detectability (224D) falls below the minimum acceptable limit (224E), an alert will be issued to drive maintenance of the sensing system.

Figures 13, 14:
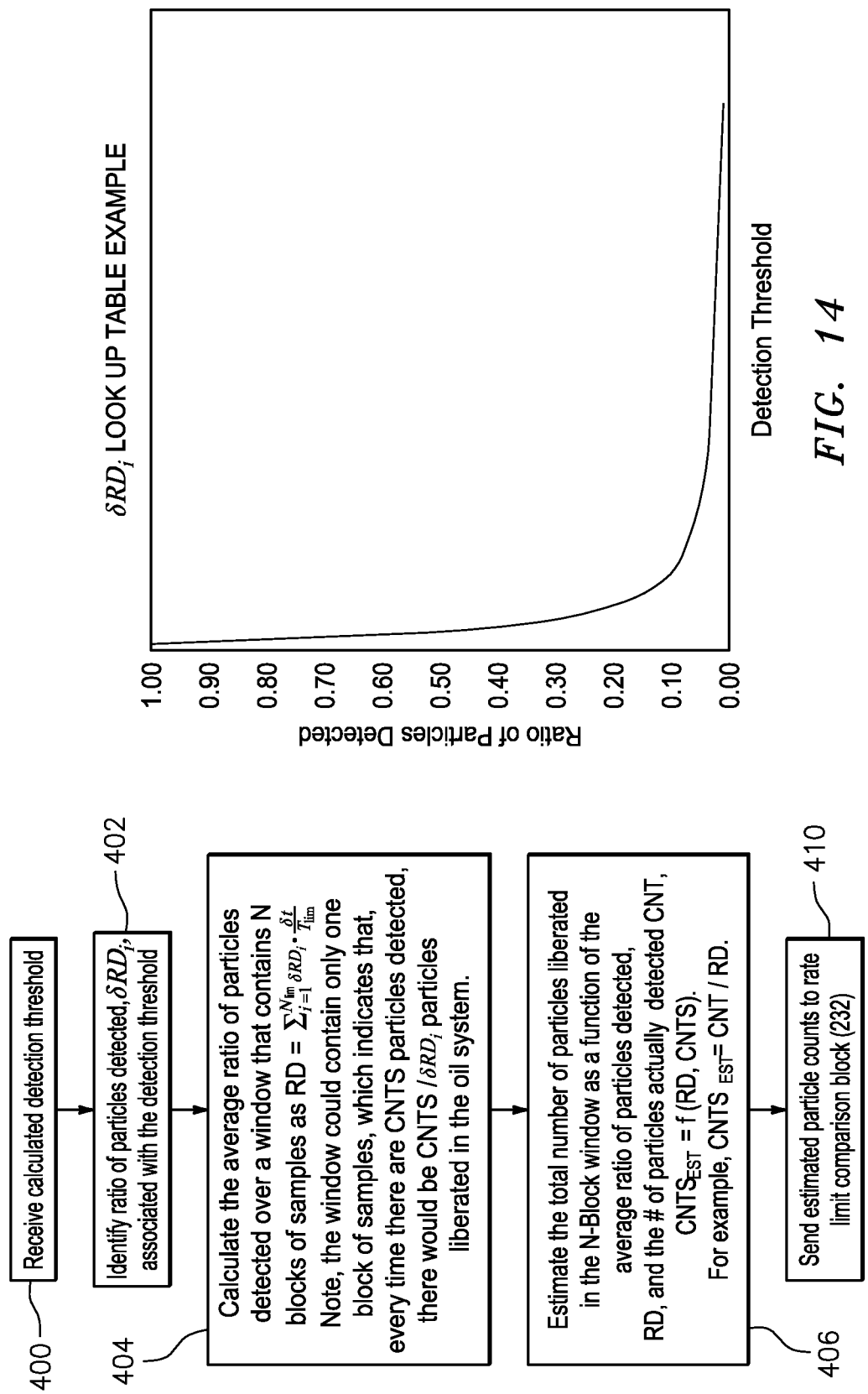
FIG. 13 is a block diagram representative of a method that estimates debris release.
FIG. 14 is a graphical representation of a detection threshold vs ratio of particle detected.
Figure 15:
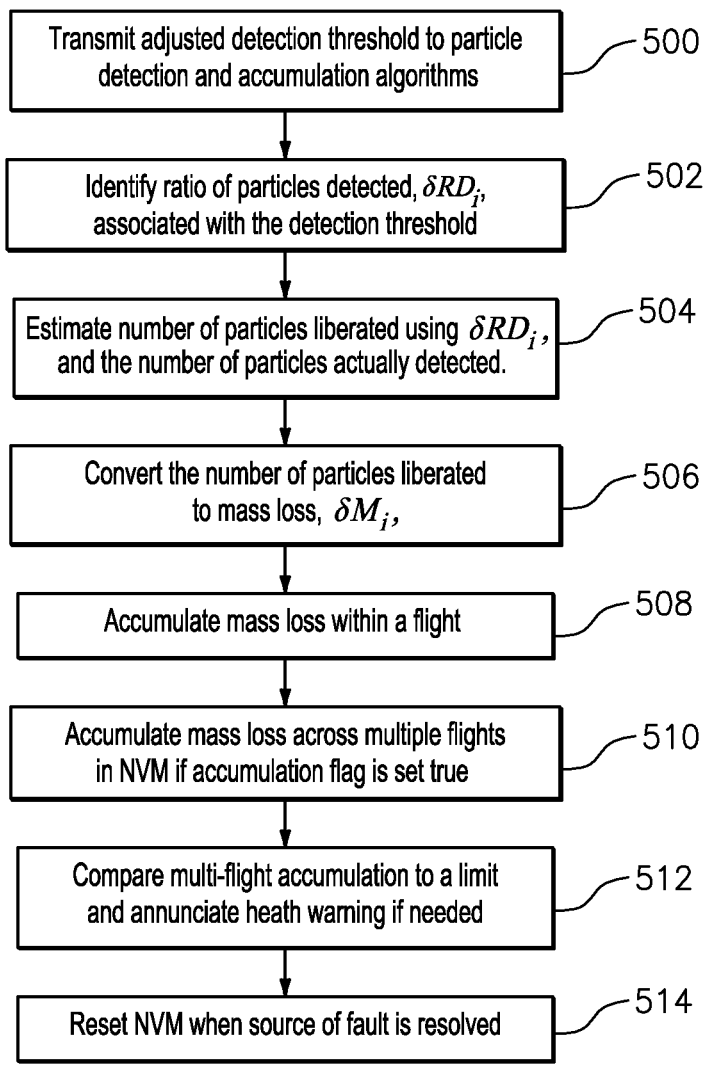
FIG. 15 is a graphical representation of a long term accumulation of particle mass detected module.
Figure 16:
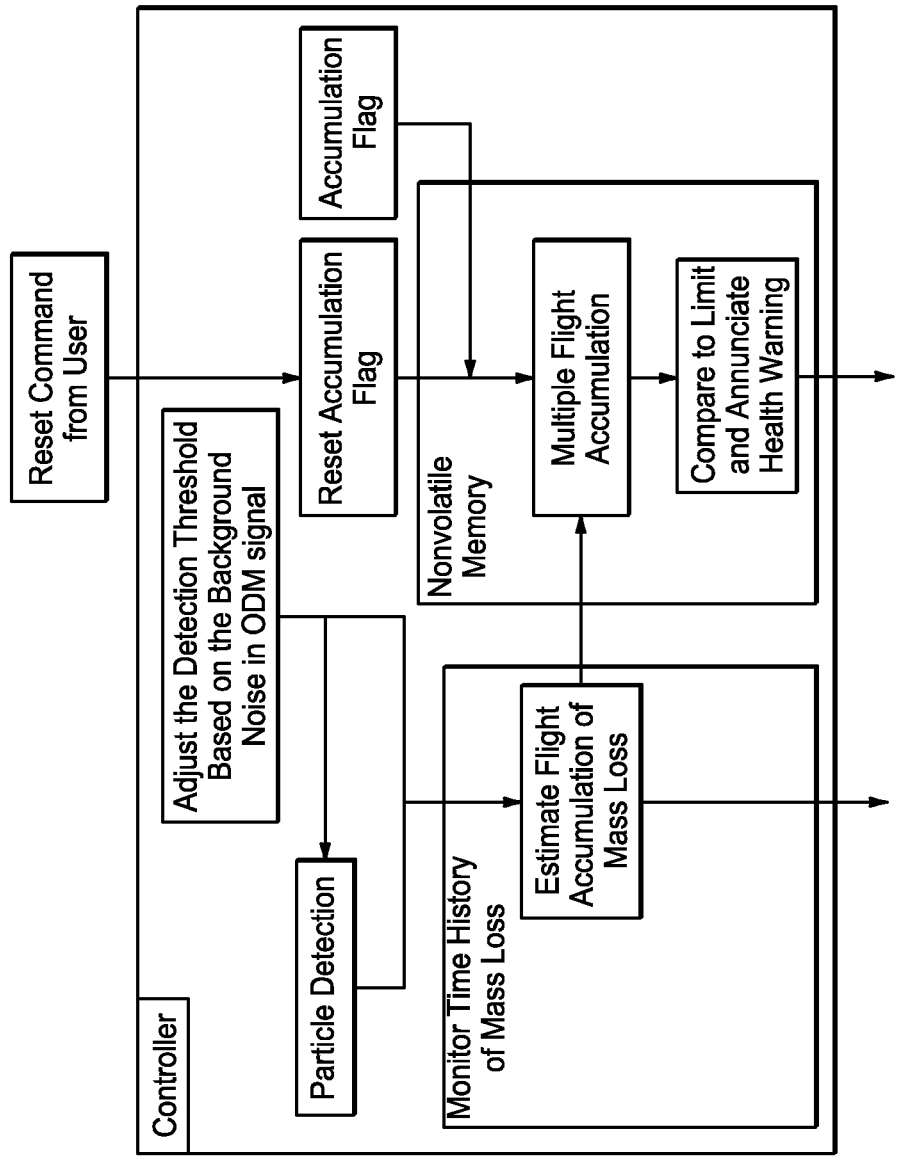
FIG. 16 is a block diagram representative of logic for the long term accumulation of particle mass detected module.

The updated detection threshold is also communicated to the particle detection algorithm ((220F); 216), a rate limit adjustment algorithm ((222F); 222; FIG. 7), detectability algorithm ((224E) 224; FIG. 8), particle estimation algorithm (400; FIG. 13), and mass accumulation algorithm (500; FIG. 15, FIG. 16).

With continued reference to FIG. 5, the controller monitors the debris detection system 110 background noise levels in real-time and dynamically calculates a particle detection threshold such that an adequate signal to noise ratio is enforced. This has the effect of ensuring relatively large particles are counted rather than missed entirely due to a detection threshold falling below background noise levels. In other words, the particle detection threshold based on the signal noise level (220) shifts the focus from debris (particle) detection to event (fault/failure) detection. The system monitors the debris detection system 110 background noise levels in real-time and dynamically calculates a particle detection threshold.

System availability (226) is calculated over time using a signal rejection time determined from the particle detection algorithm (216) and is compared to a minimum limit which results in a sensor health warning (228) if below the predetermined limit.

Alternative to rate limited reduction described in [0038], the amount of debris/particles that are unable to be detected as a result of detection threshold increase can be estimated in the time window of interest as a function of the adaptive detection threshold. The sum of such estimate and the rate of particles actually detected make the total rate of particle release (230). That is, the particle release rate (232) may be estimated utilizing the actual particle release rate increased as a function of the adaptive detection threshold to estimate missed debris. The total rate of particle release is compared to a predefined, constant minimum limit, which results in a mechanical failure alert if the limit is exceeded. The detectability may be calculated utilizing the time history data of the adaptive threshold. The detectability (224) is also calculated for comparison to a minimum limit which results in a sensor health warning (234) if below the predetermined limit.

Figure 9:
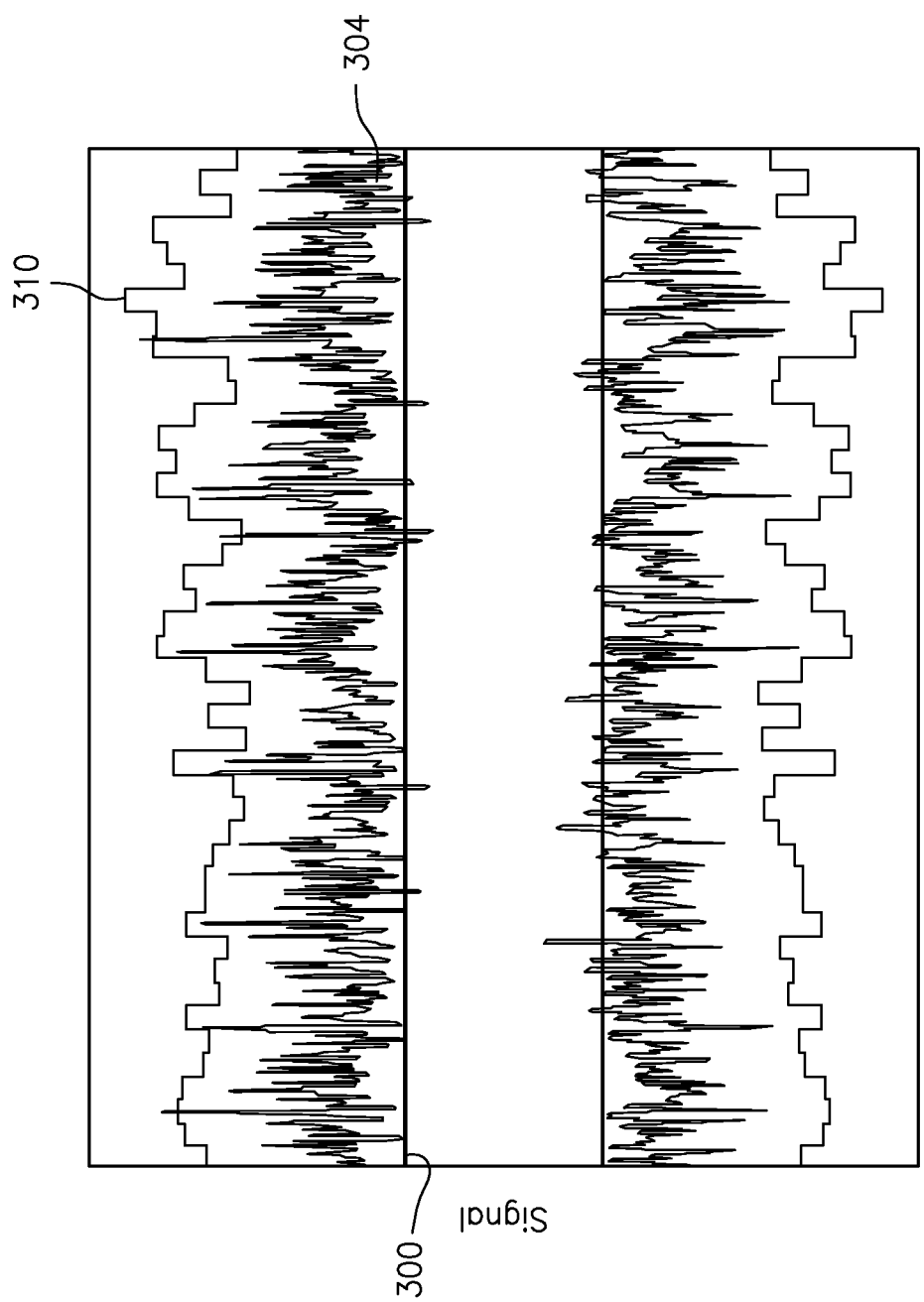
FIG. 9 is a schematic representation of a calculated detection threshold.

With reference to FIG. 9, for example, a baseline detection threshold 300 may be buried in background noise 304. When a fixed detection threshold leads to a signal to noise ratio of less than 1, the debris detection system 110 may lose the ability to detect debris, mechanical failures, and may generate nuisance particle counts. That is, the current state uses a fixed detection threshold in a particle detection algorithm to detect the particle so the detection threshold has to be crossed for the particle detection algorithm, so if there is noise consistently in excess of the detection threshold the debris detection system 110 will spend time processing and rejecting the noise even when particles are coming through the system. The availability of the debris detection system 110 with a baseline detection threshold 300 is thus essentially 0% which cannot properly detect particles.

An adaptive threshold 310 as provided by the logic 124 of the debris detection system 110 based on the signal 304 is nearly 100% above the signal and can detect particles with adequate signal to noise ratio. The threshold change is limited data frame to data frame to prevent the debris detection system 110 from reacting to an asymmetric particle, leading to a missed detection. Additional threshold change is based on the multiple peaks that are still above the detection threshold, typical of a connection issue. The further adjustment will set the detection threshold at n-th peak with n being derived from the possible particle release of a mechanical failure. If majority of the peaks are one-sided, an alert can be transmitted to indicate a possible connection issue.

Figure 10:
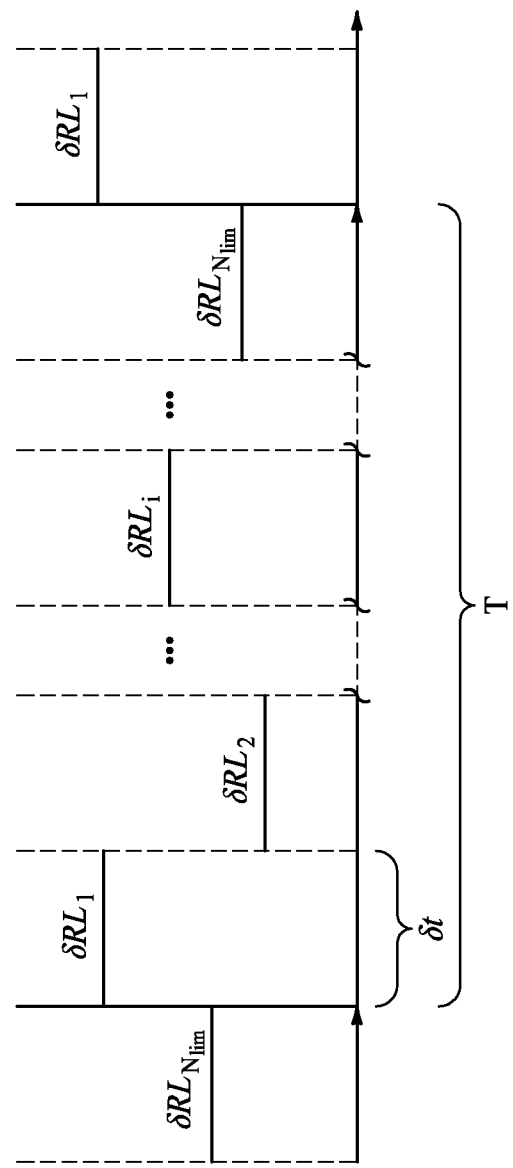
FIG. 10 is a representation of an adaptive rate limit algorithm scheme.
Figure 11:
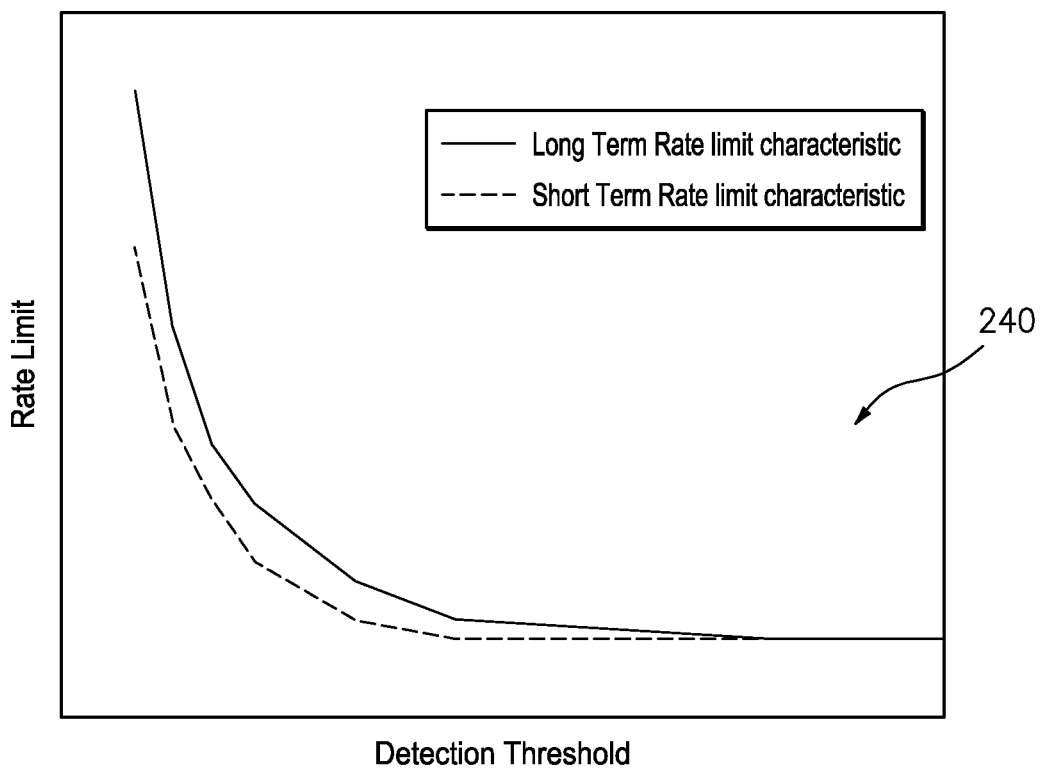
FIG. 11 is a graphical representation of a look up table example for the rate limit characteristics.

With reference to FIG. 10, the rate limit adjustment algorithm (222; FIG. 5) includes a rate limit influence factor (240; FIG. 11). The rate limit influence factor 240 is calculated by assigning a rate limit to a detection threshold, and multiplying by the ratio of the time of the processing block for which the detection threshold is computed relative to the time of the window in which the rate is computed (long term, short term). The rate limit influence factor 240 are then summed over the number of processing blocks in the window. The sum is then the new rate limit for the particle detection algorithm (216; FIG. 5).

Utilizing a noise measure to adjust the particle detection threshold, for example Root Mean Square (RMS), is effective when a particle quickly passes through the sensor, resulting in a high frequency signal that encompasses only a small portion of monitored signal but has minimal impact on the RMS algorithm. If, on the other hand, a particle passes slowly through the sensor, the impact on the RMS algorithm can be significant, presenting a risk that the threshold would be set above the particle and result in misdetection. To mitigate this risk, the change in detection threshold can be limited based on knowledge of system behavior, or a limited threshold change rate.

To prevent setting the detection threshold too low, peak counting over an RMS based threshold can be applied to set the final detection threshold. That is, the RMS based threshold will filter out the majority of the background noise without affecting the possible particle signals standing out of the noise, and the peak counting algorithm will fine-tune the detection threshold so that the final detection threshold will be above all but possible particle signals. For example, if the expected particle release rate is 5 Hz, a maximum of 2 peaks may be expected within a 200 millisecond window to be a particle. The 3rd peak can be assumed as noise, and the threshold can be set above that peak. Once the detection threshold is adjusted, the fundamental detection capability of the debris detection system 110 is changed. To prevent late detection of a failure event, the failure alert is changed accordingly. For example, if in an ideal noiseless system, the debris rate to trigger an alert is 50 particles per hour, and in a high noise system, the detection threshold is adjusted and the debris detection system 110 has lost 20% detectability, then the debris rate alert limit may be adjusted to 40 particles per hour to compensate for the detection capability loss.

Figure 12:
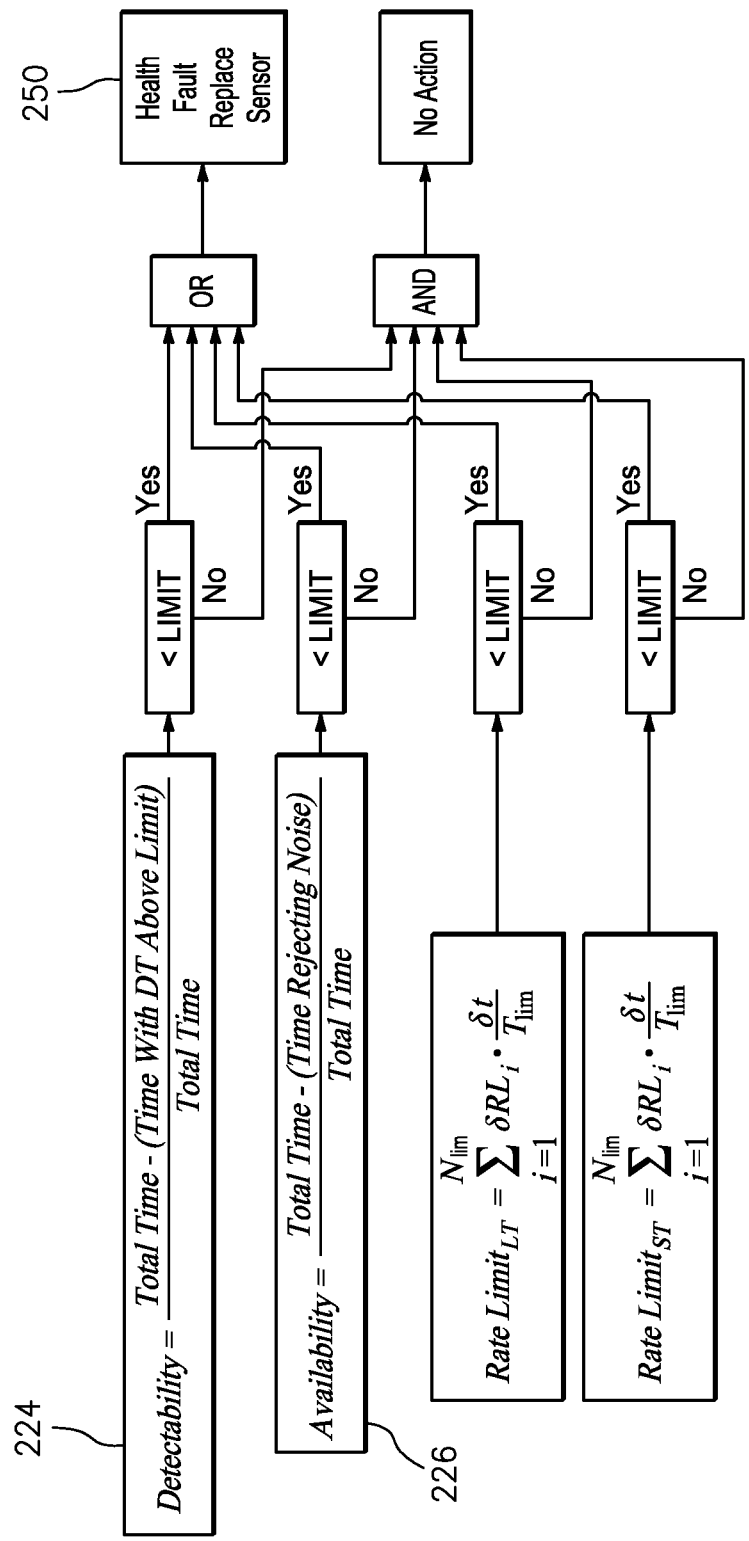
FIG. 12 is a graphical representation of health fault limits for detectability and availability.

With reference to FIG. 12, the debris detection system 110 includes algorithms for detectability (224; FIG. 5) and availability (226; FIG. 5) that are calculated to assess the time that the debris detection system 110 spends above a critical detection threshold. The detectability algorithm can be weighted by level of detection threshold (i.e. a very high detection threshold will impact detectability more than a lower but still elevated threshold).

A health fault alert for sensor replacement 250 may be provided if the rate limits are calculated critically low and/or if the debris detection system 110 spends too much time rejecting noise. This detection methodology facilitates system integrity for failure detection, namely, the debris detection system 110 compensation for background noise does not result in a detection capability loss that is too excessive to detect failure. A critical detection capability may be determined by utilizing knowledge of failure modes and retained over the engine operation. If the debris detection system 110 reduces detection capability beyond that critical point, an alert is generated such that the degraded hardware can be replaced. Furthermore, with an adaptive threshold that adapts to background noise, a rejected threshold crossing can be assumed as signal anomalies. That is, if signal anomalies lead to the debris detection system 110 spending too much time rejecting particles, the hardware should also be replaced.

As an alternative to adjustment (reduction) of the rate limit in response to the elevated detection threshold for mechanical fault alert, the rate limit could remain fixed, but the number of particles that missed being detected as a result of elevated detection threshold, and hence, the total number of particles liberated, must be estimated for comparison with the fixed rate limit.

With reference to FIG. 13, the background noise levels may also be utilized to predict mechanical systems failures through the augmentation of the particles counted rather than adjustment of the particle release rate limits. That is, the particle release rate may be estimated (232; FIG. 5). In this embodiment, knowledge of particle size distributions of expected system failure modes with respect to the calculated detection threshold ((400); 220; FIG. 6) can be used to determine a ratio of particles detected at various detection threshold levels (402; FIG. 14). Every block of data will have a unique detection threshold, and thus a unique ratio of particles detected. The ratio is defined as the number of particles actually detected with the associated detection threshold over the total number of particles supposedly detectable by the sensing system (the sum of the number of particles detected and the possible number of particles missed being detected as a result of the elevated detection threshold). For any given time window of interest that contains N blocks of samples, the average ratio of particles detected is calculated (404), and the total number of particles supposedly detected is computed as a function of the number of particles actually detected and the average ratio of particles detected. This total count can be estimated as the number of particles actually detected divided by the average ratio of the particles detected (406), and the result will be compared directly to a fixed rate limit as an alternative to the process outlined in FIG. 7 for communication to the limit comparison algorithm (410).

Detailed knowledge of the expected mechanical system and particle size distributions of failure modes allow for rate limit compensation to be optimized. While the rate alert limit is adjusted lower to compensate for the detection capability loss due to noises, the robustness of failure detection may be weakened as fewer particles are counted in the decision making. Such robustness reduction will be made up by examining particle accumulation over a longer time period of time. In other words, a failure event is detected if the rate alert limit is exceeded and a large number of particles have been accumulated in the past.

In one embodiment, window sizes of 1 hour or less are utilized to calculate release rates. This may be adequate for quick failures; however, this may be inadequate to detect slow progressing failures over multiple flights. Furthermore, particle count may not be a good metric for mechanical failure when tracked over multiple flights as size of particles matters. The corresponding mass loss of the particles is a normalized measure, and hence, setting a multi-flight mass loss accumulation and comparing it to a fixed limit provides an additional failure annunciation. Mass loss will be accumulated in the controller memory over a fixed window of time or cycles. If the limit is crossed a fault will be annunciated. If the failure is troubleshot, the capability to reset the counter is advantageous.

With reference to FIG. 15, in one embodiment, an adjusted detection threshold is then transmitted to the particle detection and accumulation algorithms (500) to identify a ratio of particles detected, $\delta RDi$, with the detection threshold (502). Then, the number of particles counted using $\delta RDi$ is estimated (504), and the particle count is converted (506) to mass loss. The accumulated mass loss within a flight (508) and the accumulated mass loss across multiple flights may be stored within the nonvolatile memory (510; FIG. 16). The multi-flight accumulation is then compared to a limit and an alert is issued if required (512). The nonvolatile memory is then reset when the source of fault is resolved (514). The mass loss is thereby estimated utilizing the actual particle release increased as a function of the adaptive detection threshold to include debris missed, and converted to mass. If the reset accumulation flag is set to true, the multiple flight accumulation in the nonvolatile memory is set to zero. The accumulation can be continuous, or begin at a defined onset of mechanical failure defined by system knowledge via the accumulation flag.

The debris detection system 110 thereby adapts oil debris monitor or other monitor technology to high background noise jet engine applications.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein; however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason, the appended claims should be studied to determine true scope and content.

What is claimed:

1. A method for determining a detection threshold used for determining the presence of a particle in a system, comprising:
   a) collecting channel data from a sensor;
   b) calculating a detection threshold based on a measure of background noise in the system;
   c) processing the channel data to identify a ferrous and nonferrous signal;
   d) processing the ferrous and nonferrous signals to determine signal peaks above the detection threshold;
   e) adjusting the detection threshold if more signal peaks are observed than allowable particles in a given time window; and
   f) transmitting the detection threshold determined in step e); and further comprising
   receiving the detection threshold, and monitoring the sensor by:
   identifying a rate limit as a function of the detection threshold;
   calculating a rate limit influence factor;
   summing a discrete rate limit influence continuously over a window to calculate the rate limit;
   transmitting the calculated rate limit to a particle release rate comparison algorithm; and
   generating an alert if the calculated rate limit is below an acceptable limit.

2. The method as recited in claim 1, further comprising converting the channel data to digital data within a controller on-board an aircraft.

3. The method as recited in claim 1, further comprising continually filling a buffer of the controller with the channel data.

4. The method as recited in claim 3, wherein the sensor is an oil debris monitor sensor.

5. The method as recited in claim 1, wherein step e) comprises transmitting the detection threshold to a particle detection algorithm.

6. The method as recited in claim 1, wherein step e) comprises transmitting the detection threshold to a rate limit algorithm.

7. The method as recited in claim 1, wherein step e) comprises transmitting the detection threshold to a detectability calculation algorithm.

8. The method as recited in claim 1, wherein step c) comprises processing the ferrous and nonferrous signals to determine signal peaks above C*RMS of the signals.

9. The method as recited in claim 8, wherein C is a calculated constant determined by analyzing system data to determine how an adjusted threshold would impact the particle detection threshold.

10. The method as recited in claim 9, wherein C is less than or equal to 4.

11. The method as recited in claim 10, wherein the RMS calculation using the raw signal data is determined in a fixed time window.

12. The method as recited in claim 1, wherein the channel data is I and Q channel data.

13. A method of monitoring a sensing system, comprising:
   receiving a calculated detection threshold;
   identifying a rate limit as a function of the calculated detection threshold;
   calculating a rate limit influence factor;
   summing a discrete rate limit influence continuously over a window to calculate the rate limit;
   transmitting the calculated rate limit to a particle release rate comparison algorithm; and
   generating an alert if the calculated rate limit is below an acceptable limit.

14. The method of claim 13, wherein the rate limit is derived from a critical release rate measured by accumulated particle count, accumulated particle mass, or combinations thereof.

15. An oil system for a gas turbine engine, comprising:
   an oil flow path;
   an in-line oil debris monitor sensor;
   a controller in communication with the in-line oil debris monitor sensor to determine whether a particle is present, a detection threshold for presence of the particle determined as a function of background noise; and a tangible, non-transitory memory configured to communicate with the controller, the tangible, non-transitory memory having instructions stored thereon that, in response to execution by the controller, perform operations comprising:

processing ferrous and nonferrous signals to determine signal peaks above a detection threshold;

adjusting the detection threshold if more signal peaks are observed than allowable particles in a given time window; and summing a discrete rate limit influence continuously over a window to calculate the rate limit.

16. The system as recited in claim 15, wherein the oil flow path is in communication with a geared architecture of the gas turbine engine.

17. The system as recited in claim 15, wherein the system will issue a health warning when the detection threshold is below a calculated value.

18. The system as recited in claim 17, wherein a rate limit is determined as a function of the detection threshold.

\* \* \* \* \*